(12) United States Patent
Both et al.

(10) Patent No.: US 6,425,420 B2
(45) Date of Patent: Jul. 30, 2002

(54) PROCEDURE DEVICE FOR THE DECANTING OF DENTAL FILLING SUBSTANCES

(75) Inventors: Adam Both, Hanau; Ulrich Kläres, Umstadt; Ralf Luckau, Kahl; Michael Roth, Mainaschaff; Udo Bauer, Nidderau, all of (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/827,319

(22) Filed: Apr. 6, 2001

(30) Foreign Application Priority Data

Apr. 7, 2000 (DE) .......................................... 110 17 476

(51) Int. Cl.⁷ .............................. B65B 1/04; B65B 3/04
(52) U.S. Cl. ................................ 141/2; 141/18; 141/27; 141/383; 433/90
(58) Field of Search ........................... 141/2, 18, 25, 141/27, 83, 94, 102, 383; 433/80, 89, 90

(56) References Cited

U.S. PATENT DOCUMENTS 3,731,453 A * 5/1973 Porteous ........................ 53/37
4,331,188 A * 5/1982 Reynaud ................. 141/311 R
4,534,150 A * 8/1985 Shirota ........................ 53/390
5,045,081 A * 9/1991 Dysarz ........................ 604/411

FOREIGN PATENT DOCUMENTS

DE  2 254 153   5/1974
EP  0 587 085   3/1994

* cited by examiner

Primary Examiner—Timothy L. Maust
(74) Attorney, Agent, or Firm—Smith, Gambrell & Russell, LLP

(57) ABSTRACT

A process and device for decanting dental filling substances (2) into special individual containers (3) for use in dental treatment. Storage container (1) is connected leakproof and pressure sealed to conically shaped jet (4) of individual container (3). By applying pressure, dental filling substance (2) is squeezed from storage container (1) through jet (4) into the container body, thereby pushing ahead of it axially movable piston (7) until same reaches a final position determined by circuit-controlled limit stop (10). Thus, a precise dosage can be guaranteed during a long service life, even while filling several individual containers (3) simultaneously. Sensor (11), placed within the range of limit stop (10), records the final position of stop rod (6) conveying the movement of piston (7).

12 Claims, 3 Drawing Sheets

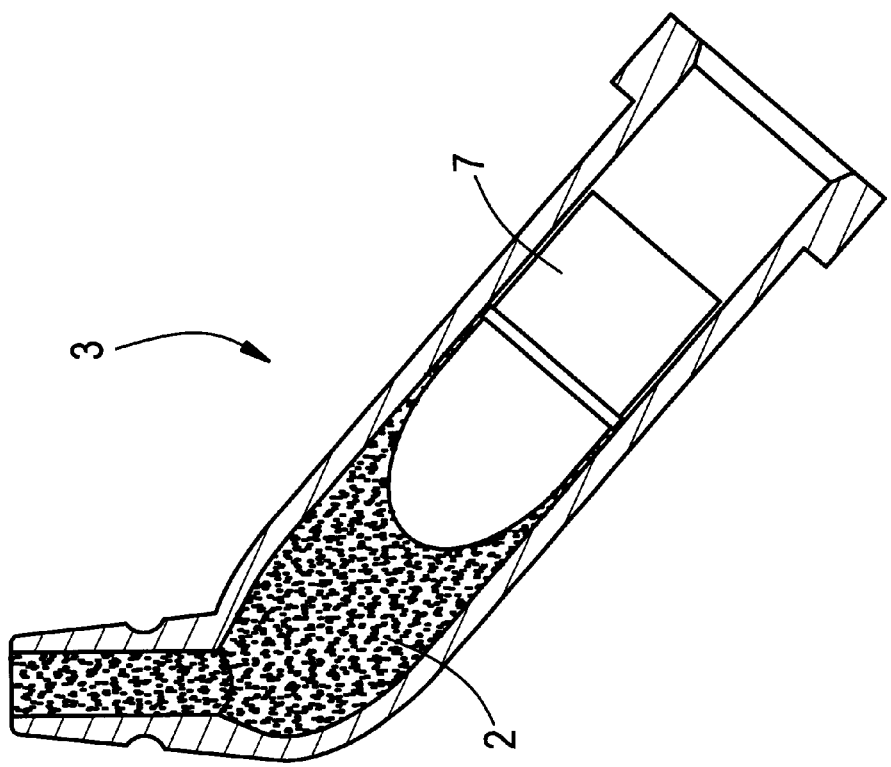
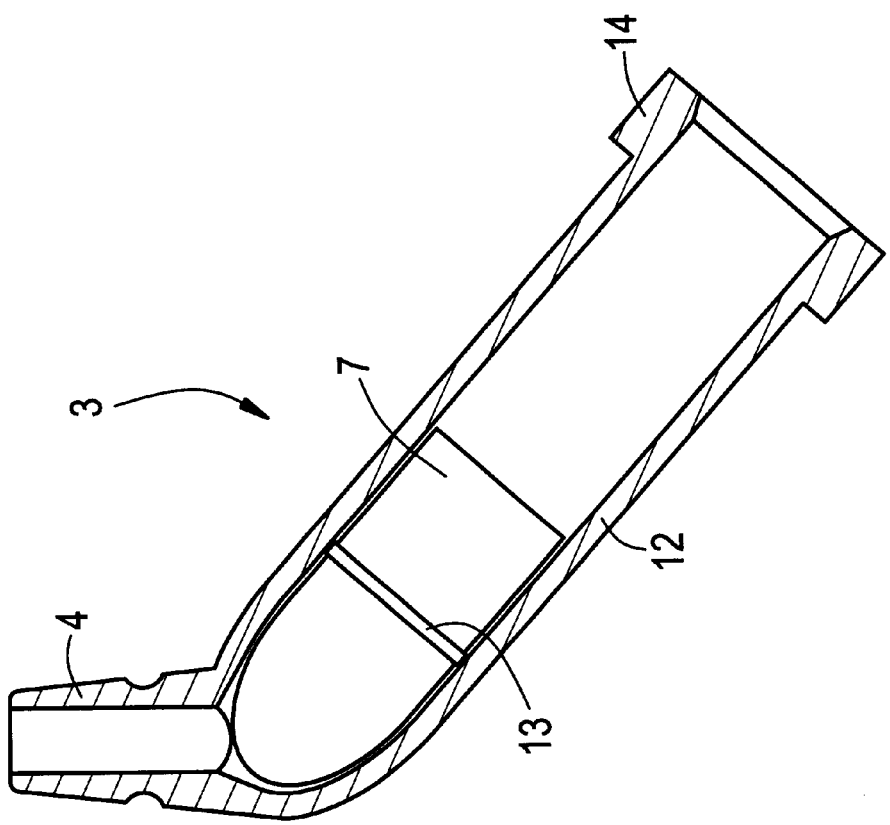

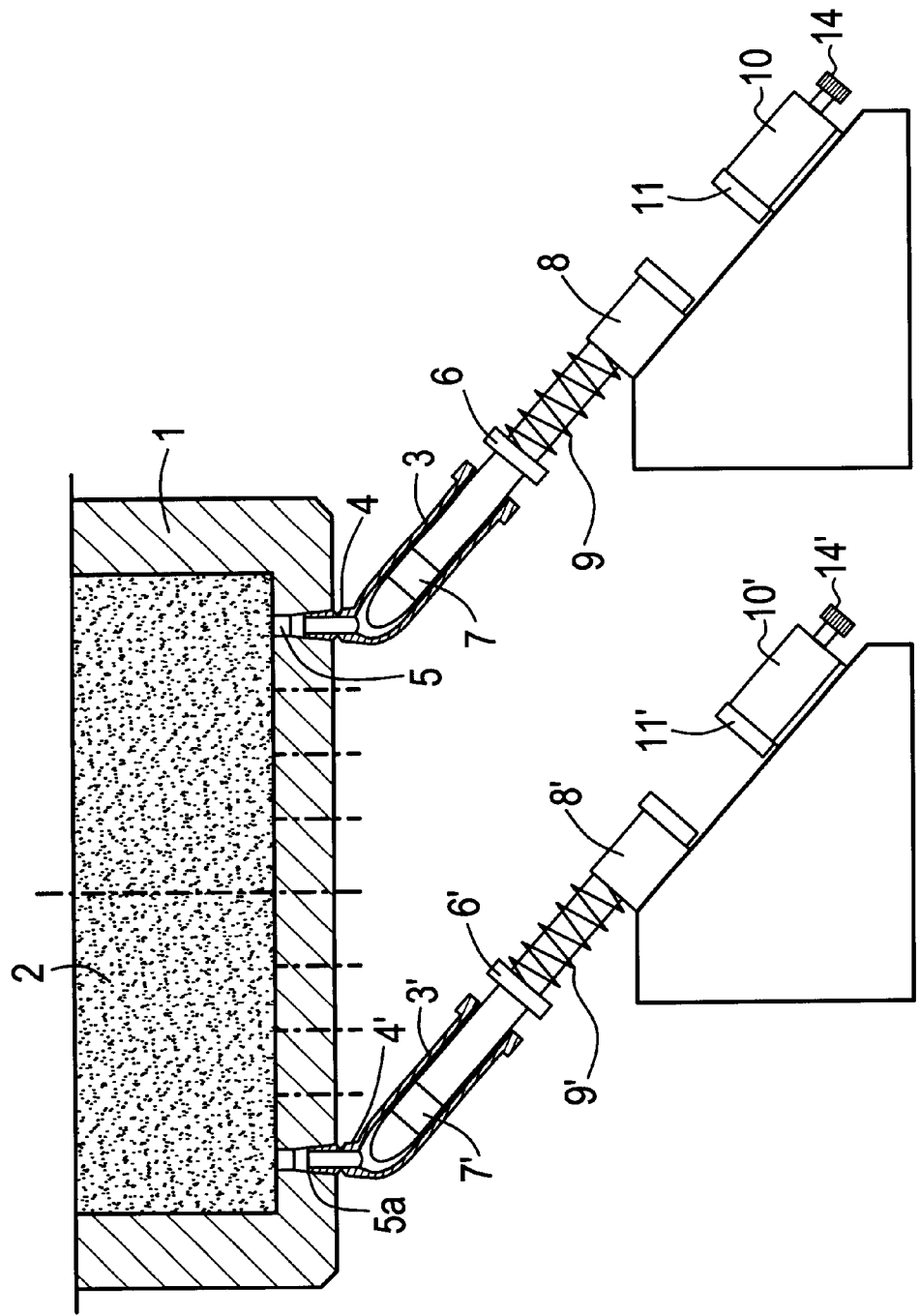

PROCEDURE DEVICE FOR THE DECANTING OF DENTAL FILLING SUBSTANCES

INTRODUCTION AND BACKGROUND

The present invention applies to a procedure for the decanting of dental filling substances from a storage container into individual containers consisting of a container body fitted with a jet at one end and an axially movable piston sealing the other end.

For use in dental practice, dental medical substances, e.g. photohardening filling substances, are packed in special individual containers that are often disposable. Such containers normally hold a quantity sufficient for one application of dental filling substance which the dentist needs to restore a prepared dental cavity.

Customary known procedures use an individual container without an integral piston, positioned in such a way that a hollow needle, protruding from the storage container for dental filling substances, reaches into the opening left by the removed piston in the individual container that has to be filled. By applying pressure, the dental filling substance is squeezed from the storage container through the hollow needle into the open individual container. In this process, the outlet of the hollow needle inside the individual container can be adjusted according to the rising level of dental filling substance in the individual container. With the decanting process completed, the individual container is sealed with the piston and a cap on the tip of the jet.

Decanting time depends on the quantity of the dental filling substance to be decanted but also on product properties, e.g. viscosity of the filling substance, and process parameters, e.g. the pressure applied while squeezing. In known decanting procedures the dental filling substance is squeezed through thin outlets that are shaped like hollow needles, from the storage container into the individual containers. Customary outlets feature a small diameter, causing decanting time to grow out of proportion with increasing viscosity of the dental filling substance, or requiring such a high pressure that detrimental effects may be suffered by the viscous filling substance. Owing to the severe strain on the outlet, this has to be made of metal for the most part or even completely. However, contact of abrasive filling substance with metal surfaces may lead to abraded particles from the outlet entering the filling substance decanted and thereby causing color changes. The practice of decanting procedures of the aforementioned kind is therefore lengthy and uneconomical especially for highly viscous, paste-like filling substances, and is fraught with disadvantages hitherto unavoidable.

An object of the invention, therefore, is to enable decanting of, dental filling substances of the aforementioned kind in a way such that highly viscous dental filling substances may also be decanted quickly and economically.

SUMMARY OF THE INVENTION

The above and other objects of the invention can be achieved by squeezing the dental filling substance through the jet into the container body while pushing the piston forward until it reaches a preset final position.

In order to perform the decanting process, the jet of the individual container is docked leakproof and pressure sealed to an outlet of the storage container. At the start of the decanting process the axially movable piston rests in the individual container close to the jet. Under pressure, dental filling substance is squeezed through the jet into the container body while pushing the piston forward ahead of it. The decanting process is finished as soon as the piston reaches a preset final position. Air trapped at the start of the decanting process in the individual container is released through the air relief profile of a piston sealing lip, which at the same time prevents an unintentional escape of dental filling substance through the individual container opening for the piston. In this way, the individual container is filled completely, and without residual air, with dental filling substance. This notably includes the jet, which, in known decanting procedures for highly viscous filling substances, is often filled only partially or not at all. As an additional advantage, filling substance exits immediately during dental treatment. So far, filling substance had to be squeezed through the initially empty jet by repeatedly actuating the applicator, before it would exit from the jet and be ready for application.

Preferably, the final position of the axially movable piston is adjustable. Via the adjustable final position of the piston, the available volume of the individual container for dental filling substance can be predetermined and the precise apportioning of the quantity decanted can be ascertained with utmost precision. In the event that a modification of the quantity of dental filling substance to be decanted should be desired, it can easily be obtained by modifying the final position of the piston.

According to a further embodiment of the invention, several individual containers can be filled simultaneously in a controlled manner through outlets in the storage container. The quantity of dental filling substance for the individual containers is determined by the correlated preset final position of the piston. No additional device is necessary for the apportioning of dental filling substance. Therefore, with comparatively little effort, many individual containers can be filled simultaneously in a precise and reproducible manner, signifying a substantial advantage concerning decanting performance and profitability.

BRIEF DESCRIPTION OF THE DRAWINGS

The present invention will be further understood with reference to the accompanying drawings, wherein:

FIG. 2 is a schematic sectional view of the individual container before being filled;

FIG. 3 is a schematic sectional view of the individual container while being filled and FIG. 4 is a schematic section view of a device for decanting dental filling substance into several individual containers, with the piston final position adjustable.

DETAILED DESCRIPTION OF THE INVENTION

Figure 1:
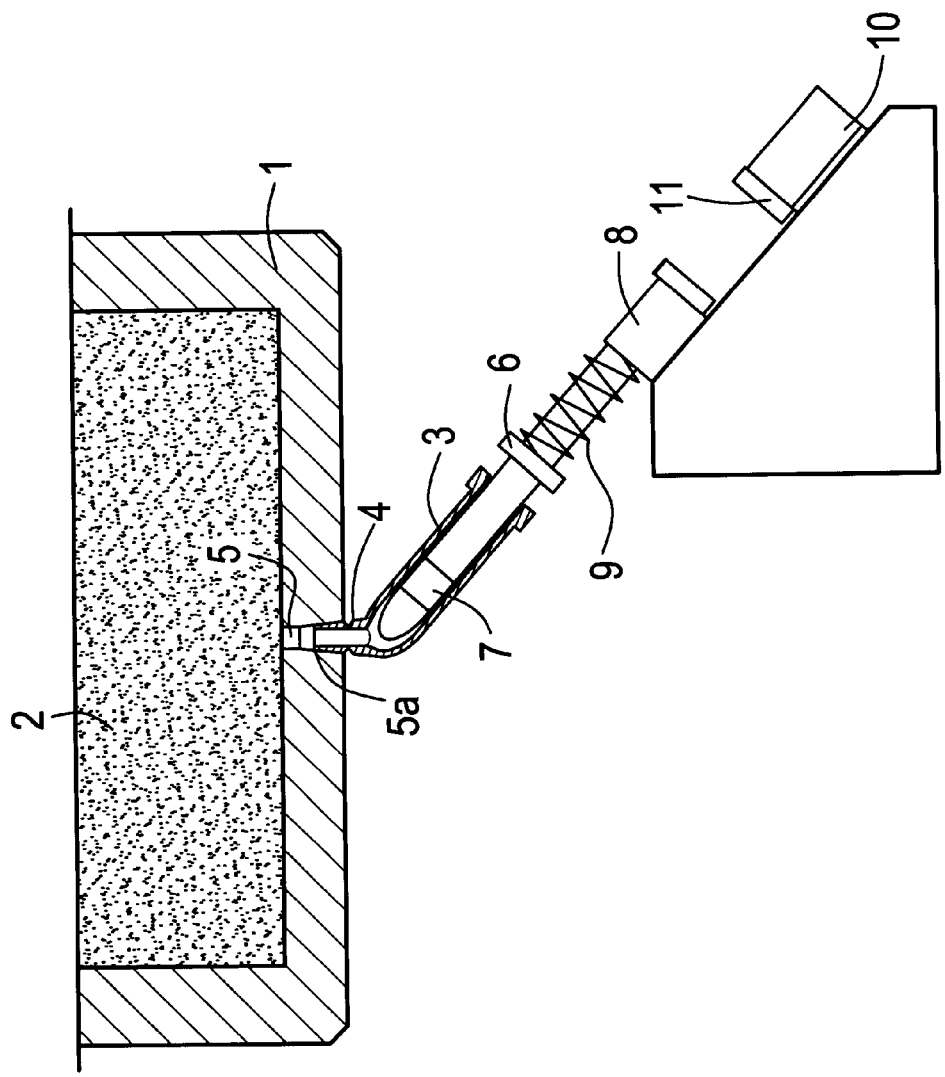
FIG. 1 is a schematic section view of a device for decanting dental filling substance into an individual container according to the invention.

According to a preferred embodiment form of the invention, the dose of dental filling substance actually filled into each individual container during one filling operation can be controlled by weighing, and the piston stroke of each subsequent filling operation can be adjusted accordingly by a control circuit. By constant adjustment of the piston final position and thereby the quantity of dental filling substance to be decanted in relation to the actually measured dose decanted during the preceding action, a constant decanting quantity of the dental filling substance can be guaranteed in a fully automatic manner even over a long period of service life.

The present invention also concerns a device for the working of a process of decanting dental filling substances. Starting out from a known device with a storage container of dental filling substance that features at least one outlet, the device according to the invention is characterized in that the outlet is configured as a leakproof and pressure sealed docking point of the storage container with the individual container as yet to be filled. It is a feature of the invention that the stroke of the piston, axially movable inside the container body, features a limit stop.

A leakproof and pressure sealed connection permits a high decanting pressure, with which the dental filling substance is squeezed out of the storage container into the individual container, and thereby significantly reduces decanting time especially for highly viscous filling substances.

Preferably the docking point in the storage container is configured as a conical bore, shape and measurements of which correspond to the external shape of the jet. Owing to both the outlet in the storage container and the jet being shaped conically, the individual container can be connected easily at the contact point. By simply pressing the individual container against the storage container during the decanting process, a stable and pressure sealed connection between storage container and individual container is assured. In addition to its conical shape, the jet may feature a centrally positioned prescribed bending point, shaped with an annular constriction and able to compensate a possible offset angle of the container positioned for decanting.

According to a preferred embodiment form, a sensor is provided in the limit stop area, which emits a signal when the piston reaches its final position determined by the limit stop. The termination of the decanting process is thus automatically initiated. When the sensor signals, the dental filling substance inside the storage container can possibly be relieved from pressure and the individual container removed from the docking point.

According to a further development of the invention, a stop rod, running on bearings and being pushed in the direction of the piston by a spring, is axially movable like the piston and can be shifted until it reaches a final position predetermined by a limit stop. Prior to the start of the decanting process, the stop rod is shifted towards the limit stop so that the individual container can be connected at the docking point for filling. Thereafter, the stop rod is shifted in the individual container, counter to the direction of the flow of the filling substance, up to the piston already in place. By checking this position, the presence of the piston can be established. The force of the spring prevents an early shifting of the stop rod to the preset final position and thus the triggering of a signal terminating the decanting process.

Preferably, the limit stop, for determining the final position of the stop rod and the piston respectively, is adjustable. Thus, with the decanting process already under way, a precise and reproducible dosage can be obtained with a minimum of extra constructive effort. By modifying the final position of the piston, little time is needed to modify the quantity desired of the correlated filling substance to be decanted, so that only short machine down-times occur for a change from one decanting weight to another.

According to a preferred embodiment of the present invention, the limit stop, determining the final position of the stop rod and the piston respectively, is controlled automatically by means of a control circuit. After one individual container has been filled, the quantity of dental filling substance actually decanted can be measured, and the final position limiting the piston stroke can be corrected according to the reading. Thus, the controlled and precise filling of many individual containers can be carried out even for a long period of running time.

The device shown in FIG. 1 features storage container 1 holding a quantity of dental filling substance 2 to be dispensed. An individual container 3 to be filled is positioned in such a way that its jet 4 connects leakproof and pressure sealed to outlet 5 of storage container 1, the outlet being shaped like a conical bore 5a. A cylindrical stop rod 6, the diameter of which about equals that of piston 7, moves in guide bearing 8 in such a way that, just like piston 7, it is movable axially within individual container 3. A spring 9 pushes stop rod 6 in the direction of jet 4 up to piston 7 located there. When, under pressure, dental filling substance 2 is squeezed from storage container 1 through outlet 5 and jet 4 into individual container 3, the increasing volume of dental filling substance 2 inside individual container 3 causes piston 7 and consequently stop rod 6 to shift against the force of the spring. First, air escapes, then the space is filled up gradually while piston 7 moves backwards. When piston 7 cannot be pushed further, the filling substance flowing in will fill the remaining space around the piston tip. A limit stop 10 defines in this direction the final position of stop rod 6 and piston 7 respectively. When reaching the preset final position, piston 7 is still inside individual container 3, sealing it tightly. With sensor 11, placed in the region of limit stop 10, the termination of the decanting process can be initiated, when stop rod 6 has reached its final position.

FIG. 2 shows individual container 3 prior to the start of the decanting process. One end of cylindrical hollow container body 12 is shaped into laterally offset jet 4. Container body 12 holds axially movable piston 7 fitted with radially projecting piston sealing lip 13 featuring an air relief profile. The end opposite jet 4 of cylindrical hollow container body 12 features radially projecting container rim 14 which improves the pressure resistance of container body 12 and positions individual container 3 during the decanting process and in the applicator.

FIG. 3 shows individual container 3 during the decanting process. Pressurized dental filling substance 2 penetrates through jet 4 into container body 12, pushing tightly sealing piston 7 forward.

The apparatus shown in FIG. 4 demonstrates simultaneous filling of several individual containers 3 and features outlets 5 of storage container 1, with details shown of only two outlets. To each outlet 5 one individual container 3, 3' is attached, tightly fitting. In each individual container 3, 3' cylindrical stop rod 6, 6' is pushed towards outlet 5, by the force of a spring 9, 9'. In the opposite direction the stroke of stop rod 6, 6' is limited by limit stop 10, 10'. This final position can be adjusted individually for each stop rod 6, 6' e.g. by modifying screw adjuster 14, 14'. Individual containers 3, 3' can each be weighed individually after one decanting process. Depending on the quantity of dental, filling substance actually decanted, such individual adjustment of the final position of corresponding stop rods 6, 6' is possible for each outlet 5.

Further variations and modifications of the foregoing will be apparent to those skilled in the art and are intended to be encompassed by the claims appended hereto.

German priority application 100 17 476.0 is relied on and incorporated herein by reference.

What is claimed is:

1. A process for the decanting of a dental filling substances from a storage container having at least one outlet into an individual container having a container body with a jet at one end and an axially removable piston sealing the other end, comprising squeezing the dental filling substance through the jet into said container body, and pushing a piston located inside said container body up to a preset final position, during said squeezing said jet of said individual container is in leak-proofed and pressure sealed engagement with said outlets.

2. The process according to claim 1, wherein the final position of axially movable piston is adjustable.

3. The process according to claim 1 further comprising filling a plurality of individual containers through respective outlets of the storage container, and simultaneously controlling said filling.

4. The process according to claim 3, further comprising decanting a dose of dental filling-substance into each individual container in a controlled manner by weighing after one decanting operation, and before a subsequent decanting operation, adjusting each corresponding piston stroke according by means of a control loop.

5. A device for the decanting of a dental filling substance comprising a storage container for holding a supply of dental filling substance to be filled into at least one individual container having a container body with a jet at one end and an axially movable piston sealing. the other end, having at least one outlet being a leakproof and, pressure sealed docking point of the storage container and in mating engagement with said individual container that is to be filled, said piston being limited by limit stop arranged in the same axis as said piston.

6. The device according to claim 5, wherein the docking point takes the shape of a conical bore in storage container, whose shape and measurements corresponding to the outer shape of said jet.

7. The device according to claim 5, further comprising a sensor placed near limit stop which triggers a signal when piston reaches its final position determined by limit stop.

8. The device according to claim 5, wherein a stop rod axially movable like piston, running on bearings in a guide and being pushed in the direction of piston by means of spring can be shifted until reaching a final position determined by limit stop.

9. The device according to claim 8, wherein the limit stop, determining the final position of stop rod and piston respectively, is adjustable.

10. The device according to claim 8, wherein the limit stop, determining the final position of stop rod and piston is controlled automatically by means of a control loop.

11. The device according to claim 10, wherein the limit stop, determining the final position of stop rod and piston is controlled automatically by means of a control loop.

12. A process for the decanting of a dental filling substances from a storage container having at least one outlet into an individual container having a container body with a jet at one end and an axially movable piston sealing the other end, comprising squeezing the dental filling substance through the jet into said container body, and pushing a piston located inside said container body up to a preset final position, during said squeezing said jet of said individual container is in leak-proofed and pressure sealed engagement with said outlets, filling a plurality of individual containers through respect outlets of the storage containers, said filling being simultaneously controlled and decanting a dose of dental filling substance into each individual container in a control manner by weighing after one decanting operation and before a subsequent decanting operation, arid adjusting each corresponding piston stroke accordingly by means of a control loop.

* * * * *

UNITED STATES PATENT AND TRADEMARK OFFICE
CERTIFICATE OF CORRECTION

PATENT NO. : 6,425,420 B2
DATED : July 30, 2002
INVENTOR(S) : Adam Both et al.

It is certified that error appears in the above-identified patent and that said Letters Patent is hereby corrected as shown below:

<u>Title page, Item [54] and Column 1, lines 1-3,</u>
Please correct the title to read as follows:

-- **PROCEDURE AND DEVICE FOR THE
  DECANTING OF DENTAL FILLING SUBSTANCES** --

Item [30], please correct the Foreign Application Priority Data, to read as follows:

-- Apr. 7, 2000  (DE)         100 17 476 --

Signed and Sealed this

Twenty-second Day of April, 2003

JAMES E. ROGAN
*Director of the United States Patent and Trademark Office*